United States Patent [19]

Azria et al.

[11] Patent Number: 5,759,565

[45] Date of Patent: Jun. 2, 1998

[54] GALENIC COMPOSITIONS COMPRISING CALCITONIN AND THEIR USE

[75] Inventors: Moise Azria, Basel; Thomas Cavanak, Biel-Benken, both of Switzerland

[73] Assignee: Novartis Corporation, Summit, N.J.

[21] Appl. No.: 815,457

[22] Filed: Dec. 31, 1991

Related U.S. Application Data

[63] Continuation of Ser. No. 503,206, Apr. 2, 1990, abandoned, which is a continuation of Ser. No. 334,664, Apr. 6, 1989, abandoned, which is a continuation of Ser. No. 145,803, Jan. 19, 1988, abandoned, which is a continuation of Ser. No. 34,114, Apr. 1, 1987, abandoned, which is a continuation of Ser. No. 820,491, Jan. 17, 1986, abandoned, which is a continuation of Ser. No. 723,748, Apr. 16, 1985, abandoned, which is a continuation of Ser. No. 627,845, Jul. 5, 1984, abandoned, which is a continuation of Ser. No. 537,356, Sep. 29, 1983, abandoned.

[30] Foreign Application Priority Data

| Oct. 5, 1982 | [GB] | United Kingdom | 8228390 |
| Dec. 30, 1982 | [GB] | United Kingdom | 8236928 |
| Aug. 3, 1983 | [GB] | United Kingdom | 8320865 |
| Aug. 22, 1983 | [GB] | United Kingdom | 8322528 |

[51] Int. Cl.⁶ .............. A61K 9/08; A61K 9/12; A61K 38/23

[52] U.S. Cl. .............. 424/434; 424/400; 514/2; 514/21; 514/808; 514/970; 514/975

[58] Field of Search ................. 424/400, 434, 424/43, 41; 514/2, 21, 808, 970, 975

[56] References Cited

U.S. PATENT DOCUMENTS

| 4,241,051 | 12/1980 | Christie | 424/177 |
| 4,954,342 | 9/1990 | Lattanzi | 424/436 |
| 4,988,512 | 1/1991 | Azria | 424/422 |

FOREIGN PATENT DOCUMENTS 25197   9/1981   Japan.

OTHER PUBLICATIONS

Ziegler. Acta Endocrinol Suppl 215, pp. 54–55 1978.
Van de Donk. Chem. Abstr. 95, 1981 #2149335.

*Primary Examiner*—Gollamudi S. Kishore
*Attorney, Agent, or Firm*—Carol A. Loeschorn

[57] ABSTRACT

Pharmaceutical compositions for nasal administration comprising i) a calcitonin, and ii) benzalkonium chloride, and/or iv) a surfactant, suitable for application to the nasal mucosa, in iii) a liquid diluent or carrier, suitable for application to the nasal mucosa. The compositions are suitably adapted for administration in the form of a nasal spray.

20 Claims, 1 Drawing Sheet

FIGURE

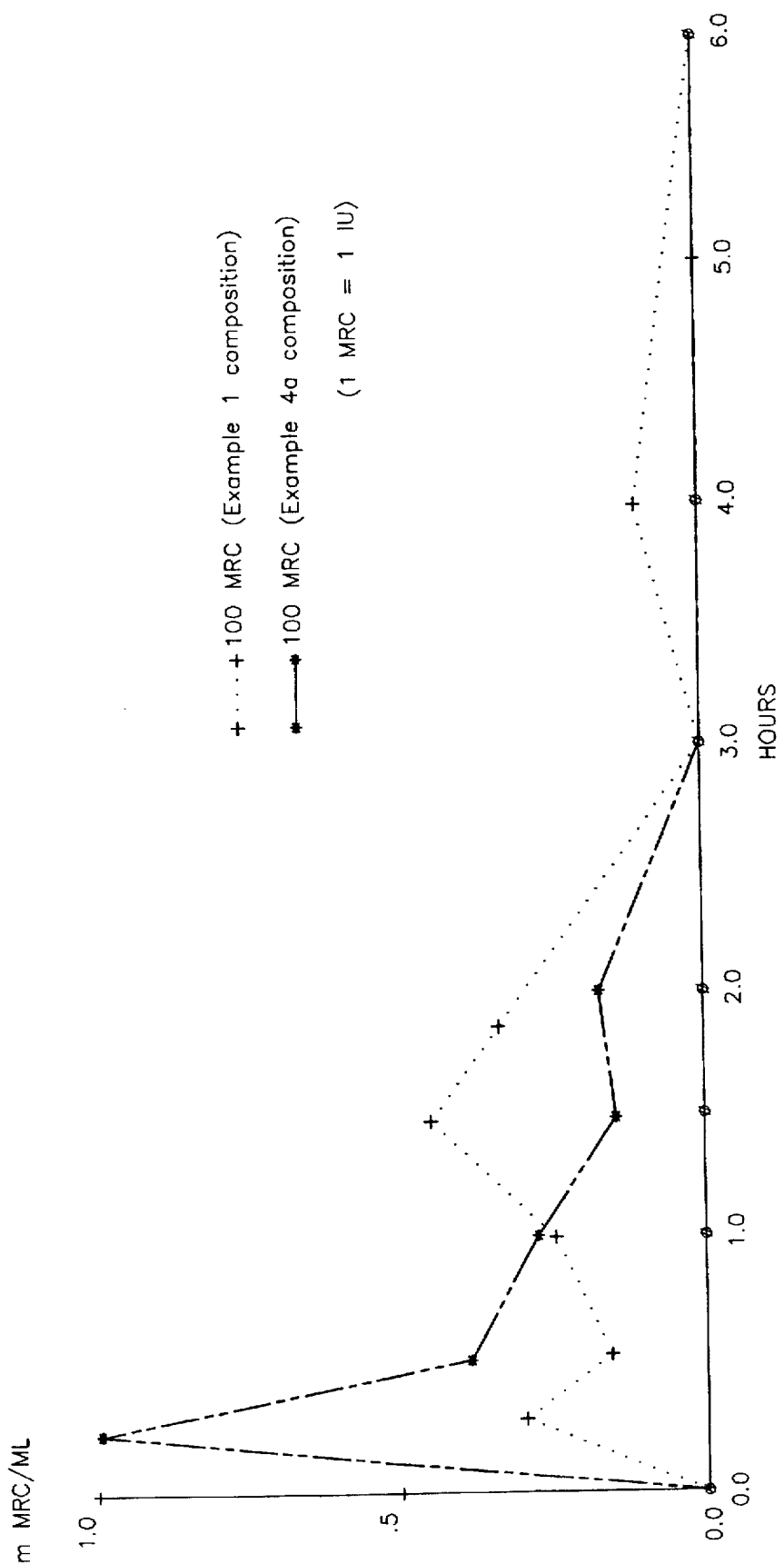

GALENIC COMPOSITIONS COMPRISING CALCITONIN AND THEIR USE

This is a continuation of application Ser. No. 07/503,206, filed Apr. 2, 1990, now abandoned, which in turn is a continuation of application Ser. No. 07/334,664, filed Apr. 6, 1989, now abandoned, which in turn is a continuation of application Ser. No. 07/145,803, filed Jan. 19, 1988, now abandoned, which in turn is a continuation of application Ser. No. 07/034,114, filed Apr. 1, 1987, now abandoned, which in turn is a continuation of application Ser. No. 06/820,491, filed Jan. 17, 1986, now abandoned, which in turn is a continuation of application Ser. No. 06/723,748, filed Apr. 16, 1985, now abandoned, which in turn is a continuation of application Ser. No. 06/627,845, filed Jul. 5, 1984, now abandoned, which in turn is a continuation of application Ser. No. 06/537,356 filed Sep. 29, 1983, abandoned.

The present invention relates to novel galenic compositions comprising a calcitonin as active ingredient.

The calcitonins comprise a known class of pharmaceutically active, long-chain polypeptides of varying, well documented pharmaceutical utility. Various calcitonins, including e.g. salmon and eel calcitonin, are commercially available and commonly employed in the treatment of e.g. Paget's disease, hypercalcaemia and osteoporosis.

As is commonly the case with polypeptides however, provision of convenient and effective means of administering calcitonins has presented many difficulties. Being polypeptides, the calcitonins are susceptible to degradation on administration and only pass with difficulty into the body fluids. For this reason parenteral administration has hitherto been the only route commonly available which permits effective treatment. Generally administration is by injection. Such means of administration are always inconvenient and when administration is to be effected at regular intervals can cause considerable pain to the patient. The finding of viable alternative means of administration causing less discomfort to the patient and preferably allowing ready self-application while at the same time achieving bio-availability levels sufficient for effective treatment in clinic has accordingly remained, for many years, a major goal. We have now found that it is possible to provide effective clinical treatment with calcitonins by administration via the nasal route, i.e. by application to the nasal mucosa. More particularly we have found that in accordance with the particular teachings of the present invention, calcitonin bio-availability levels equivalent to those obtained on administration of standard intramuscular doses can be achieved on nasal administration at dosage levels which are fully within the limits of tolerability and practicability. It has further been found that the fish calcitonins and their derivatives e.g. salmon calcitonin and the eel calcitonin derivative 1,7-Asu-eel calcitonin, herein referred to as Elcatonin, and in particular salmon calcitonin, are especially suited for application via the nasal route in accordance with the teachings of the invention.

The nasal route provides a simple and painless mode of administration which may be easily carried out by the patient himself, for example administering a nasal spray or drop solution from a nasal applicator. This route is clearly of great advantage over parenteral administration which has generally to be given under medical supervision.

While administration via the nasal route will clearly be preferable to parenteral administration, e.g. injection, as hitherto commonly practiced, the provision of a composition suitable for use for a nasal dosage form itself presents many difficulties. One problem, especially acute in relation to nasal administration of complex pharmaceutical agents such as the calcitonins, is that of providing a fully compatible and effective means for avoiding contamination e.g. by pathogenic or other undesired micro-organisms. Provision of an appropriate active-ingredient-compatible and effective preserving agent to protect against contamination is especially critical for a nasal pharmaceutical composition where the risk of contamination is particularly high. The preserving agent must suffice to provide not only for initial contamination avoidance, e.g. during formulation and filling of the composition into its container, but continued contamination avoidance during use particularly where multiple dosaging from a single container/applicator is required. In particular problems arise where e.g. a nasal applicator is, as is often the case, subsequently stored for months before use. During this phase the selected preserving agent may be rendered useless, e.g. by absorption onto the inside surfaces of the applicator, by heat-degradation, or, where the preserving agent is to any degree unduly volatile, as a consequence of leakage from the applicator. Further, during the actual phase of use (and where multiple dosaging from a single applicator is foreseen this may extend over a period of several days or weeks), there is danger that the applicator may leak or otherwise let in unwanted micro-organisms or other contaminants from the outside atmosphere generally, or from the nostrils. Moreover the composition may be subjected to brief periods of elevated temperature, e.g. during transport or storage.

In addition to the above mentioned difficulties a pharmaceutical composition developed for nasal application must at the same time be appropriately tolerated in particular at the immediate site of application. It should, for example, neither cause irritation to the nasal mucosa (e.g. should cause no significant prickling sensation) nor cause significant reduction of the ciliary beating frequency.

Very many well-known preserving agents present themselves for possible use in calcitonin pharmaceutical compositions. However experiment has shown that not all are suitable for practical use in relation to a calcitonin nasal spray. Thus chlorbutanol at 0.6% in calcitonin nasal pharmaceutical compositions showed insufficient activity against the test fungus *Pen. steckii*, more than 3 days being required to reduce the cell count to less than 0.1%. Moreover, chlorbutanol was found to attack rubber stoppers and other joints used in nasal spray applicators between the spray pump and a bottle.

Chlorbutanol additionally caused at 0.6% more than 50% inhibition of the ciliary beating frequency of rat trachea within 20 minutes according to the microphotooscillographic method of L. Chevance et al. Acta Otolaryng. 70, 16:28 (1970). These are just some of the disadvantageous effects that can be encountered.

In accordance with the present invention it has now been surprisingly found that pharmaceutical compositions can be obtained comprising a calcitonin as active ingredient which meet the high standards of stability and tolerability required for nasal application and which are, for example, eminently suitable for use in multiple dose nasal spray applicators, i.e. applicators capable of delivering a series of individual dosages over e.g. period of several days or weeks, by the use of benzalkonium chloride as a co-ingredient and preserving agent. Surprisingly it has also been found that use of benzalkonium chloride, even at the very low concentration required for use as a preserving agent, may confer beneficial advantages in relation to the nasal resorption characteristics of calcitonin containing compositions and hence enhance calcitonin bio-availability levels consequential to nasal application.

In accordance with the foregoing the present invention provides, in a first aspect, a pharmaceutical composition for nasal administration, comprising:

i) a calcitonin, and ii) benzalkonium chloride, in iii) a liquid diluent or carrier, suitable for application to the nasal mucosa.

BRIEF DESCRIPTION OF THE DRAWINGS

The FIGURE is a graphical comparison of the salmon calcitonin plasma levels in two groups of Rhesus monkeys after each group is nasally administered 100 MRC units of different calcitonin compositions according to the instant invention.

The term "calcitonin" is used throughout the present specification and claims in a broad sense to include not only the naturally occurring calcitonins, but also their pharmaceutically active derivatives and analogues, e.g. in which one or more of the peptide residues present in the naturally occurring product is replaced, or in which the N- or C-terminal is modified.

Preferred calcitonins for use in accordance with the invention are salmon, human and porcine calcitonins and Elcatonin. All of these compounds are commercially available and have been extensively described, together with their pharmaceutical properties, in the literature.

As previously indicated it has been found that exceptionally good results, e.g. in terms of bio-availability levels and duration of presence in the blood plasma, are obtained on nasal administration of salmon calcitonin. Salmon calcitonin is accordingly the most preferred calcitonin for use in accordance with the invention.

As will be appreciated the calcitonins for use in the invention may be in free form or in pharmaceutically acceptable salt or complex form, e.g. in pharmaceutically acceptable acid addition salt form. Such salts and complexes are known and possess an equivalent degree of activity and tolerability to the free forms. Suitable acid addition salt forms for use in accordance with the invention include e.g. the hydrochlorides and acetates.

Benzalkonium chloride is the name commonly employed for known mixtures of quaternary ammonium salts typically of the generalized formula $C_6H_5-CH_2-NR(CH_3)_2Cl$, wherein R is $C_8H_{17}$ to $C_{18}H_{37}$. A preferred concentration for the benzalkonium chloride component in the compositions of the invention is from about 0.002 to about 0.02, typically about 0.01% (w/v) of the total composition.

The above defined compositions may be applied in accordance with the invention to the nasal mucosa e.g. either in drop or in spray form. As hereinafter described however, they are most preferably applied in spray form, i.e. in the form of finely divided droplets.

The compositions of the invention may of course also include additional ingredients, in particular components belonging to the class of conventional pharmaceutically applicable surfactants. In this connection it has in accordance with a further aspect of the present invention been found that the use of surface active agents generally in relation to the nasal application of calcitonins, in particular salmon calcitonin, may increase resorption via the nasal mucosa and hence improve obtained bio-availablity rates. Accordingly in a further aspect the present invention also provides a composition adapted for administration in the form of a liquid nasal spray, comprising:

i) a calcitonin, and iv) a surfactant suitable for application to the nasal mucosa, in iii) a liquid diluent or carrier suitable for application to the nasal mucosa.

Preferably the liquid diluent or carrier (iii) for use in the compositions of the invention [i.e., whether comprising ii) benzalkonium chloride and/or iv) a conventional surfactant as a necessary component] will comprise water (pharmaceutical grade). Most preferably it comprises aqueous saline. The compositions of the invention are formulated so as to permit administration via the nasal route. For this purpose they may also contain, e.g. minimum amounts of any additional ingredients or excipients desired, for example, additional preservatives or e.g. ciliary stimulants such as caffeine. Generally for nasal administration a mildly acid pH will be preferred. Preferably the compositions of the invention have a pH of from about 3 to 5, most preferably from about 3.5 to about 4.5. Adjustment of the pH is achieved by addition of an appropriate acid, such as hydrochloric acid.

The compositions of the invention should also possess an appropriate isotonicity and viscosity. Preferably they have an osmotic pressure of from about 260 to about 380 mOsm/liter. Desired viscosity for the compositions of the invention will depend on the particular form for administration, e.g. whether administration is to be by nasal drops or nasal spray. For nasal drops an appropriate viscosity is from about 2 to about $40 \times 10^{-3}$ Pa.S.. For nasal sprays the viscosity will suitably be less than $2 \times 10^{-3}$ Pa.S., e.g. from 1 to $2 \times 10^{-3}$ Pa.S.

Where compositions in accordance with the invention comprise a conventional surfactant (whether or not they also comprise benzalkonium chloride) non-ionic surfactants are preferred. Especially preferred surfactants are polyoxyalkylene higher alcohol ethers, e.g. of the general formula (I)

$$RO + (CH_2)_n - O \}_x H \qquad (I)$$

wherein RO is the residue of a higher alcohol especially a higher alkanol or alkylphenol, such as lauryl or cetyl alcohol, or a sterol residue, especially a lanosterol, dihydrocholesterol or cholesterol residue, as well as mixtures of two or more such ethers. Preferred polyoxyalkylene ethers for use in accordance with the invention are polyoxyethylene and polyoxypropylene ethers (i.e. wherein n in the formula above is 2 or 3) in particular polyoxyethylene and polyoxypropylene lauryl, cetyl and cholesteryl ethers as well as mixtures of two or more such ethers.

The hydroxy group at the end alkylene unit of such ethers as aforesaid may be partially or completely acylated, by e.g. acyl residues of aliphatic carboxylic acids, such as acetic acid.

Preferred ethers for use in accordance with the invention have a hydrophilic-lipophilic balance (HLB group number) of from about 10 to about 20, especially from about 12 to about 16.

Especially suitable ethers for use in accordance with the invention are those wherein the average number of repeating units in the polyoxyalkylene moiety (x in the formula above) is from 4 to 75, suitably 8 to 30, more especially 16 to 26. The ethers may be obtained in accordance with known techniques. A wide variety of such products are commercially available and e.g. offered for sale e.g. by the company Amerchol under the trade-name Solulan®, the companies KAO Soap, ICI and Atlas under the trade-names Emalex®, Brij® and Laureth® and from the company Croda under the trade-name Cetomacrogol®.

Examples of polyoxyalkylene ethers suitable for use in accordance with the invention are as follows: (POE= polyoxyethylene ether; POP=polyoxypropylene ether; x=average No. of repeating units in the POP/POE moiety).
1. Cholesteryl ethers:
 1.1 Solulan® C-24-POE, x=24.
2. Ethers of Lanolin alcohols:
 2.1 Solulan® 16-POE, x=16.
 2.2 Solulan® 25-POE, x=25.
 2.3 Solulan® 75-POE, x=75.
 2.4 Solulan® PB-10-POE, x=10.
 2.5 Solulan® 98-POE, x=10—partially acetylated.
 2.6 Solulan® 97-POE, x=9—fully acetylated.
3. Lauryl ethers:
 3.1 Emalex® 709/Laureth® 9-POE, x=9.
 3.2 Laureth® 4/Brij® 30-POE, x=4.
 3.3 Laureth® 23/Brij® 35-POE, x=23.
4. Cetyl ethers:
 4.1 Cetomacrogol®-POE, x=20 to 24.

Lanolin alcohols are also known as wool fat alcohols and are a mixture of cholesterol, dihydrocholesterol and lanosterol.

Preferred ethers for use in accordance with the present invention are polyoxyethylene cholesteryl ethers, i.e. of the above formula I, wherein n=2 and RO is a cholesterol residue, especially such ethers wherein the number of repeating units in the polyoxyethylene moiety is from 16 to 26, most preferably about 24.

More preferably such ethers are substantially free from contaminents in particular from other polyoxyalkylene ethers. Most preferably they comprise at least 75%, more preferably at least 85%, and most preferably at least 90% by weight of pure polyoxyethylene cholesteryl ether.

When a surfactant, e.g. a polyoxyalkylene ether is employed, the amount present in the compositions of the invention will vary depending on the particular surfactant chosen, the particular mode of administration (e.g. drop or spray) and the effect desired. In general, however, the amount present will be of the order of from about 2.0 to about 200 (preferably to about 100, more preferably to about 20), suitably from about 5 to about 30 (preferably to about 15), and most preferably about 10 mg/ml.

The amount of calcitonin to be administered in accordance with the method of the invention and hence the amount of active ingredient in the composition of the invention will, of course, depend on the particular calcitonin chosen, the condition to be treated, the desired frequency of administration and the effect desired.

As indicated in the following example 2, bio-availability for calcitonins, in particular salmon calcitonin, as determined in terms of blood-plasma concentration following nasal administration in accordance with the teachings of the present invention has been found to be surprisingly high, generally of the order of ca. 50% of levels achieved on intra-muscular injection. Accordingly administration in accordance with the invention will appropriately be effected so as to give a dosage rate of the order of 2× or more, e.g. from about 2 to 4× the dosage rate required for treatment via intra-parietal, e.g. intra-muscular, administration.

Hitherto, where calcitonin, e.g. salmon calcitonin, treatment has been effected by intra-muscular injection, individual dosages of ca. 50 to 100 MRC units are applied at a rate of from ca. 1× daily to ca. 3× weekly. For nasal administration in accordance with the present invention, treatment will therefore suitably comprise administration of dosages of from about 50 to about 400 MRC units, more preferably from about 100 to about 200 MRC units at a frequency of from about 1× daily to about 3× weekly. Conveniently dosages as aforesaid will be administered in a single application, i.e. treatment will comprise administration of single nasal dosages comprising about 50 to about 400 MRC units, preferably about 100 to about 200 MRC units, calcitonin. Alternatively such dosages may be split over a series of e.g. 2 to 4 applications taken at intervals during the day, the dosage at each application then comprising about 10 to about 200, preferably about 25 to about 100 MRC units.

The total composition quantity administered at each nasal application suitably comprises from about 0.05 to 0.15 ml, typically about 0.1 ml e.g. 0.09 ml. Compositions for use in accordance with the invention accordingly suitably comprise from about 150 to about 8,000, preferably from about 500 to about 4,000, more preferably from about 500 to about 2,500, and most preferably from about 1,000 to about 2,000 MRC units calcitonin, e.g. salmon calcitonin, per ml.

For the purposes of nasal administration, the compositions of the invention will preferably be put up in a container provided with means enabling application of the contained composition to the nasal mucosa, e.g. put up in a nasal applicator device. Suitable applicators are known in the art and include those adapted for administration of liquid compositions to the nasal mucosa in drop or spray form. Since dosaging with calcitonins should be as accurately controlled as possible use of spray applicators for which the administered quantity is susceptible to precise regulation will generally be preferred. Suitable administrators include e.g. atomizing devices, e.g. pump-atomizers and aerosol dispensers. In the latter case, the applicator will contain a composition in accordance with the invention together with a propellant medium suitable for use in a nasal applicator. The atomizing device will be provided with an appropriate spray adaptor allowing delivery of the contained composition to the nasal mucosa. Such devices are well known in the art.

The container, e.g. nasal applicator, may contain sufficient composition for a single nasal dosaging or for the supply of several sequential dosages, e.g. over a period of days or weeks. Quantities of individual dosages supplied will preferably be as hereinbefore defined.

In accordance with the foregoing the present invention further provides:
A. A container containing a pharmaceutical composition for nasal administration comprising
 i) a calcitonin, and
 ii) benzalkonium chloride, in
 iii) a liquid diluent or carrier, suitable for application to the nasal mucosa,
 said container being provided with means enabling application of the contained composition to the nasal mucosa, preferably in spray form;
B. An applicator device containing a pharmaceutical composition and provided with means enabling application of the contained composition to the nasal mucosa in spray form, said contained composition comprising
 i) calcitonin, and
 iv) a surfactant suitable for application to the nasal mucosa, in
 iii) a liquid diluent or carrier suitable for application to the nasal mucosa;
 as well as
C. A method of administering a calcitonin to a subject requiring calcitonin treatment, which method comprises administering a composition for nasal administration comprising components i), ii) and iii) as defined under A above, or comprising components i), iv) and iii) as defined under B above, to said subject via the nasal route.

Containers/applicator devices as defined under A and B above are suitably nasal aerosol applicators. Preferably they enable application of the contained composition in individual fixed quantities of from about 0.05 to about 0.15 ml, e.g. about 0.1 ml.

Suitable composition as well as individual components (i), (ii), (iii) or (iv) for use in relation to the containers/applicator devices/methods defined under A, B and C above are as hereinbefore described. Suitable dosaging regimens for use in relation to the method C of the invention are also as hereinbefore described.

In addition to the foregoing the present invention also provides a method for the production of a liquid pharmaceutical composition for nasal administration comprising i) a calcitonin, and ii) benzalkonium chloride, and/or iv) a surfactant suitable for application to the nasal mucosa, in iii) a liquid diluent or carrier suitable for application to the nasal mucosa, which method comprises bringing component (i) together with component (ii) and/or component (iv) into intimate admixture, e.g. into solution in component iii), and when required introducing the obtained composition into a container provided with means enabling application of the said obtained composition to the nasal mucosa, suitably enabling application of the said obtained composition to the nasal mucosa in spray form.

The stability of the compositions of the invention may be determined in conventional manner.

The calcitonin content of the compositions of the invention under an inert nitrogen atmosphere will degrade less than 10% in 2 years at 20° C. as indicated by standard analytical tests.

For example the nasal spray composition of Example 1 hereinafter described was stored for 2 months at 5° C., 20° C. and 30° C. under nitrogen in a glass container. No detectable (less than 1%) degradation of calcitonin was observed at 5° C. and 20° C. At 30° C. a 4% degradation was observed this being no more than expected for a pure aqueous solution. These results indicate adequate stability, i.e. less than 10% degradation over 2 years under nitrogen in a sealed-container.

Also the compositions of the invention containing benzalkonium chloride are stable towards contamination by germs, e.g. according to standard tests, e.g. according to the procedures set out in S. Urban et al, Zbl. Bakt. Hyg. I Abt. Orig.B. 1972, 478–484 (1981) and S. Urban, Acta Pharm. Technol.22, 247–253 (1976). For example the cell count of standard bacteria, namely *E. coli* ATCC 8739, *Pseud. aeruginosa* ATCC 9027, *Staph. aureus* ATCC 6538, *Strept. pyogenes* ATCC 8668, and standard fungi *Cand. albicans* ATCC 10231, *Sacch. cerevisae* ATCC 9763, *Aspergillus niger* ATCC 16404 and *Pen. steckii* ATCC 10499 following innoculation of the composition will be reduced to 0.1% or less within 24 hours as indicated by standard tests.

In one stability test the nasal spray composition of Example 1 hereinafter was stored at 30° C. for 3 months under a nitrogen atmosphere in a glass container. *Pseud. aeruginosa* ATCC 9027, *Staph. aureus* ATCC 6538, *Strept. pyogenes* ATCC 8668 and the fungi *Cand. Albicans* ATCC 10231, *Sacch. cerevisae* ATCC 9763, *Aspergilles niger* ATCC 16404 and *Pen. stechii* ATCC 10499 were added to give a cell count of ca. $2 \times 10^5$ organisms in the inoculated liquid. Within 2 hours the cell count had decreased to less than 0.1%. Within 4 weeks no cells could be detected.

Moreover the compositions are well tolerated as indicated in standard tests, e.g. in that less than 50% inhibition of ciliary beating frequency is observed up to 20 minutes after administration, according to the microphoto-oscillographic method of L. Chevance et al, Acta Otolaryng. 70, 26–28 (1970).

Insignificant or no prickling sensation and a good stability against contamination during use, may also be demonstrated in standard clinical testing.

The following examples illustrate the invention.

EXAMPLE 1

Composition Containing Salmon Calcitonin Suitable for Nasal Administration

| Ingredient | Quantity (per ml) |
|---|---|
| 1) Salmon calcitonin (active ingredient) | 0.1375 mg |
| 10% excess | 0.01375 mg |
| | 0.15125 mg |
| 2) NaCl | 7.5 mg |
| 3) Benzalkonium chloride | 0.1 mg |
| 4) HCl (1 N) | added to pH 3.7 |
| 5) Distilled water | to an end volume of 1.0 ml. |

Components 1 to 3 are combined under protection of nitrogen gas (on a scale to produce a final volume of 2500 ml) in conventional manner, with 10% of salmon calcitonin being added to allow for loss at filtration. 4) is then added to bring the pH to 3.7 and distilled water added to an end-volume of 2500 ml. The obtained solution is filtered (e.g. using a 0.2 μm filter) to give a composition suitable for nasal application and for filling into a spray nasal dispenser with a solution volume of 2 ml. The composition comprises ca. 550 MRC-units active ingredient/ml, and the applicator delivers a quantitiy comprising 55 units per actuation.

EXAMPLE 2

Relative Bio-Availability Study: Nasal Administration/Intra-Muscular Injection of Salmon Calcitonin The study is conducted with 12 healthy volunteers, 6 male and 6 female, with a body weight of from 50 to 85 kg. Each subject receives 4 administrations of salmon calcitonin, one intra-muscularly and 3 nasally. Administration is effected at the following dosages:

A. Nasal:
 A1. 55 MRC units.
 A2. 110 MRC units.
 A3. 220 MRC units.
B. Intra-muscular:
 50 MRC units.

Nasal administration is effected using composition in accordance with example 1 and a spray-applicator delivering 55 MRC units per individual spray dosage. For the purposes of administration the subject is laid on the back with the head tilted backwards for 5 minutes. The nostrils are cleaned by blowing of the nose immediately prior to administration.

Intra-muscular administration is effected by injection of a single 1 ml dose of a composition similar to that of example 1, but omitting benzalkonium chloride and containing 50 MRC units into the glutaeus medius muscle.

Each subject receives the 4 administrations in randomized sequence, and at least 3 days are allowed between consecutive administrations. Each administration is effected in the morning after a light breakfast from which milk, butter and cheese is excluded. 100 ml water or orange juice is taken hourly following treatment to maintain urinary output. Further food is allowed not earlier than 4 hours after treatment.

Blood samples are taken immediately prior to administration (control), and at intervals of 5, 15, 30, 60, 90, 120, 180, 240, 360 and 480 minutes following administration. For the control a 20 ml sample is taken. All subsequent samples are 2 ml samples.

The concentration of salmon calcitonin in each serum sample is measured by radio-immuno-assay. Blood-pressure is controlled during the course of the trial and urine-samples tested for possible adverse reaction. Occurrence of side-effects, e.g. symptoms of nausea, is noted.

The AUC ("area under curve") for salmon calcitonin plasma concentration is calculated statistically, once employing all value, including those below the 26 pg/ml detectability limit, once with values below the detectability limit read as zero. Maximal plasma concentration and time at which this is reached are also determined. Relative bio-availability for nasal administration is determined from the relative dosage-standardized AUC (i.e. based on 50 MRC units) following nasal and intra-muscular administration.

Results obtained indicate that AUC values following administration of both 110 and 220 MRC units intra-nasally, are comparable with AUC values obtained following administration of 50 MRC units i.m., with serum levels for salmon calcitonin remaining above the detectability limit for 8 hours following nasal application of 110 MRC units as compared with 6 hours following i.m. application of 50 MRC units. No adverse side-effects were recorded following nasal administrations, even at the highest dosage of 220 MRC units.

EXAMPLE 3

Compositions Containing Salmon Calcitonin Suitable for Nasal Administration

| Composition No. | Quantity of salmon calcitonin employed |
|---|---|
| 3a | 0.06875 mg/ml |
| 3b | 0.275 mg/ml |
| 3c | 0.55 mg/ml |
| 3d | 1.1 mg/ml |

The compositions are prepared analogously to example 1 employing the same quantities of components 2) and 3) (7.5 mg or 0.1 mg/ml respectively), identical adjustment to pH 3.7 employing component 4) and topping up to the required end-volume employing component 5). The obtained compositions comprise ca. 250 (composition 3a), 1000 (3b), 2,000 (3c) and 4,000 (3d) MRC-units active ingredient/ml and are filled into an nasal spray dispensor delivering 0.2 ml active ingredient per actuation [=25, 100,200 and 400 MRC units/actuation for compositions 3a, 3b, 3c and 3d respectively]. It will of course be appreciated that where salmon calcitonin preparations of different activity are employed, differing quantities may be required to achieve the required concentration as defined in terms of MRC-units.

EXAMPLE 4

Compositions Containing Salmon Calcitonin Together with a Non-Ionic Surfactant Suitable for Nasal Administration The compositions are prepared in analogous manner to example 1 but with the addition of the following ingredients:

| Composition | Additional Ingredient | Quantity |
|---|---|---|
| 4a | polyoxyethylene cholesteryl ether: x = 24 | 30 mg/ml |
| 4b | polyoxyethylene cholesteryl ether: x = 24 | 10 mg/ml |
| 4c | polyoxyethylene cetyl ether: x = 20 to 24 | 100 mg/ml |

The compositions are put up in a nasal applicator as described in Example 1.

EXAMPLE 5

Comparative Bio-Availability Study for the Compositions of Examples 1 and 4a 0.2 ml portions of composition 1 or 4a were administered nasally by means of a nasal spray applicator to Rhesus monkeys (0.1 ml/nostril) giving a dosage rate of ca. 100 MRC units salmon calcitonin/monkey, and salmon calcitonin plasma levels were measured in the subsequent 6 hours. 3 runs were conducted per composition, and the combined results plotted graphically. Results (c.f. graph following) indicate that the bio-availability for both compositions (area under curve) is substantially equivalent, with the peak maximum being achieved somewhat earlier in the case of the composition of Example 4a.

We claim:

1. A liquid pharmaceutical composition comprising 1) a pharmaceutically acceptable, aqueous liquid nasal carrier; 2) a therapeutically effective amount of a calcitonin or a pharmaceutically acceptable acid addition salt thereof, wherein said calcitonin is selected from the group consisting of salmon calcitonin, human calcitonin, porcine calcitonin and 1,7-Asu-eel calcitonin; and 3) about 0.002% to about 0.02% on a weight per volume basis of a benzalkonium chloride, said composition being in a form suitable for nasal administration.

2. A composition according to claim 1 for administration in the form of a spray and having a viscosity of less than $2 \times 10^{-3}$ Pa.S.

3. A composition according to claim 1 wherein said composition is in the form of a nasal spray.

4. A composition according to claim 1 wherein said carrier comprises aqueous saline.

5. A composition according to claim 1 wherein said calcitonin, or salt is present in an amount of from about 100 to about 8,000 MRC units/ml.

6. A composition according to claim 1 wherein said calcitonin, or salt is present in an amount of from about 500 to about 4,000 MRC units/ml.

7. A composition according to claim 1 -wherein said calcitonin, or salt is present in an amount of from about 500 to about 2,500 MRC units/ml.

8. A composition according to claim 1 wherein said calcitonin, or salt is present in an amount of from about 1,000 to about 2,000 MRC units/ml.

9. A composition according to claim 1 wherein said calcitonin is salmon calcitonin.

10. A composition according to claim 1 comprising a non-ionic surfactant.

11. A composition according to claim 1 comprising a polyoxyethylene or polyoxypropylene ether.

12. A composition according to claim 1 comprising a polyoxyalkylene lauryl, cetyl, lanosteryl, dihydrocholesteryl or cholesteryl ether.

13. A composition according to claim 1 comprising a polyoxyethylene lauryl, cetyl or cholesteryl ether.

14. A composition according to claim 13 comprising a polyoxyethylene cholesteryl ether in which the number of repeating units in the polyoxyethylene moiety is from 16 to 26.

15. A composition according to claim 10 wherein said surfactant is present in an amount of from about 2.0 to about 200 mg/ml.

16. A composition according to claim 10 wherein said surfactant is present in an amount of from about 5 to about 15 mg/ml.

17. A composition according to claim 1 having a pH of from about 3 to about 5.

18. A composition according to claim 17 having a pH of from about 3.5 to 4.5.

19. A composition according to claim 17 comprising hydrochloric acid as the means to obtain the desired pH.

20. A composition according to claim 1 having an osmotic pressure of from about 260 to 380 mOsm/liter.

* * * * *

UNITED STATES PATENT AND TRADEMARK OFFICE
CERTIFICATE OF CORRECTION

PATENT NO. : 5,759,565
DATED : June 2, 1998
INVENTOR(S) : Moise Azria, et. al.

It is certified that error appears in the above-identified patent and that said Letters Patent is hereby corrected as shown below:

Title page, item [73], Assignee: change "novartis Corporation, Summit, N.J." to --Novartis AG, Basel, Switzerland--

Signed and Sealed this

Fourteenth Day of December, 1999

Attest:

Attesting Officer

Q. TODD DICKINSON

Acting Commissioner of Patents and Trademarks

Disclaimer

5,759,565—Moise Azria, Basel; Thomas Cavanak, Beil-Benken, both of Switzerland. GALENIC COMPOSITIONS COMPRISING CALCITONIN AND THEIR USE. Patent dated June 2. 1998. Disclaimer filed August 29, 2000, by the assignee, Novartis AG.

The term of this patent shall not extend beyond the expiration date of Pat. No. 5,733,569.
(*Official Gazette* December 26, 2000)